(12) United States Patent
Maeda et al.

(10) Patent No.: US 9,662,081 B2
(45) Date of Patent: May 30, 2017

(54) X-RAY CT IMAGE PROCESSING METHOD, X-RAY CT IMAGE PROCESSING PROGRAM, AND X-RAY CT IMAGE DEVICE

(71) Applicant: NATIONAL UNIVERSITY CORPORATION KYOTO UNIVERSITY, Kyoto (JP)

(72) Inventors: Shinichi Maeda, Kyoto (JP); Daigo Yoshikawa, Kyoto (JP); Takumi Tanaka, Kyoto (JP); Shin Ishii, Kyoto (JP)

(73) Assignee: Kyoto University, Kyoto (JP)

( * ) Notice: Subject to any disclaimer, the term of this patent is extended or adjusted under 35 U.S.C. 154(b) by 38 days.

(21) Appl. No.: 14/891,303

(22) PCT Filed: May 15, 2014

(86) PCT No.: PCT/JP2014/002571
§ 371 (c)(1),
(2) Date: Nov. 13, 2015

(87) PCT Pub. No.: WO2014/185078
PCT Pub. Date: Nov. 20, 2014

(65) Prior Publication Data
US 2016/0120493 A1    May 5, 2016

(30) Foreign Application Priority Data

May 15, 2013   (JP) .................. 2013-102646

(51) Int. Cl.
*G06K 9/00* (2006.01)
*A61B 6/00* (2006.01)
(Continued)

(52) U.S. Cl.
CPC ............ *A61B 6/5205* (2013.01); *A61B 6/032* (2013.01); *A61B 6/5258* (2013.01);
(Continued)

(58) Field of Classification Search
None
See application file for complete search history.

(56) References Cited

U.S. PATENT DOCUMENTS

| 9,129,431 B2 | 9/2015 | Maeda et al. |
| 2007/0269013 A1* | 11/2007 | Liu ............. G01N 23/087 378/119 |

(Continued)

FOREIGN PATENT DOCUMENTS

| JP | 2009-118887 A | 6/2009 |
| JP | 2011-156302 A | 8/2011 |
| JP | 2013-005840 A | 1/2013 |

OTHER PUBLICATIONS

Joseph A. O'Sullivan, and Jasenka Benac, "Alternating Minimization Algorithms for Transmission Tomography", IEEE Transactions on Medical Imaging, vol. 26, No. 3 (2007), pp. 283-297.
(Continued)

*Primary Examiner* — Hadi Akhavannik
(74) *Attorney, Agent, or Firm* — Ogilvie Law Firm

(57) ABSTRACT

This invention provides an X-ray CT image processing method that allows more flexible expression by expressing X-ray absorption coefficients probabilistically, makes it possible to acquire reconstructed images that are comparable to those obtained by conventional methods but involve lower X-ray doses, and can reduce beam-hardening artifacts. A probability distribution for the observation of projected X-rays is set and statistical inference is performed. Said probability distribution is expressed in terms of the process of observing a multiple-X-ray sum resulting from multiple projected X-rays being incident upon a detector. Bayesian inference in which the expected value of the posterior distribution is used for statistical inference is performed on the basis of a prior distribution for X-ray absorption coefficients, said prior distribution having parameters for the
(Continued)

material and the observation process in terms of which the multiple-X-ray sum is expressed.

9 Claims, 6 Drawing Sheets

(51) Int. Cl.
*A61B 6/03* (2006.01)
*G06T 11/00* (2006.01)

(52) U.S. Cl.
CPC .......... *G06T 11/005* (2013.01); *G06T 11/006* (2013.01); *G06T 11/008* (2013.01); *A61B 6/4241* (2013.01); *G06T 2207/10081* (2013.01); *G06T 2211/416* (2013.01)

(56) References Cited

U.S. PATENT DOCUMENTS

| | | | | |
|---|---|---|---|---|
| 2011/0243382 | A1* | 10/2011 | Morton | A61B 6/032 382/103 |
| 2012/0207272 | A1* | 8/2012 | Runft | A61J 3/074 378/57 |
| 2012/0239310 | A1* | 9/2012 | Ouvrier-Buffet | G01N 23/087 702/32 |
| 2012/0321039 | A1* | 12/2012 | Bare | G01N 23/2206 378/49 |
| 2013/0110438 | A1* | 5/2013 | Rinkel | G01N 23/087 702/85 |

OTHER PUBLICATIONS

Idris A. Elbakri and Jeffrey A. Fessler, Senior Member, IEEE, "Statistical Image Reconstruction for Polyenergetic X-Ray Computed Tomography", IEEE Transactions on Medical Imaging, vol. 21, No. 2 (2002), pp. 89-99.

Joseph A. O'Sullivan, Bruce R. Whiting, Donald L. Snyder, and Orville A. Earl, "Image Reconstruction from Data Acquired With an X-Ray Computerized Tomographic System Having Energy-Integrating Detectors", available from <<http://dls-website.com/documents/energy_integrating_2Column.pdf>>, no later than May 15, 2014, 6 pages.

Chye Hwang Yan, Robert T. Whalen, Gary S. Beaupre, Shin Y. Yen, and Sandy Napel, "Reconstruction Algorithm for Polychromatic CT Imaging: Application to Beam Hardening Correction", IEEE Transactions on Medical Imaging, vol. 19, No. 1, (2000), 11 pages.

A J Coleman and M Sinclair, "A beam-hardening correction using dual-energy computed tomography", Phys. Med. Biol., 1985, vol. 30, No. 11, (1985), pp. 1251-1256.

Jeffrey A. Fessler, Idris Elbakri, Predrag Sukovic, Neal H. Clinthorne, "Maximum-likelihood dualenergy tomographic image reconstruction", Medical Imaging 2002: Image Processing, Milan Sonka, J. Michael Fitzpatrick, 38 Editors, Proceedings of SPIE vol. 4684 (2002), pp. 38-49.

Joonki Noh, Jeffrey A. Fessler Paul E. Kinahan, "Statistical Sinogram Restoration in Dual-Energy CT for PET Attenuation Correction", IEEE Trans Med Imaging, (2009) pp. 1688-1702.

Y.Yamazaki, N. Toda, "Dual-Energy X-ray CT noise reduction algorithm under low exposure environment", IEICE Technical Report MBE2008-113, (2009), pp. 101-106.

Ruhrnschopf, E. P., G. Schwierz, et al. (1981). "Nonlinearity and Inhomogenity Effects in Computerized Tomography Due to the Exponential Attenuation of Radiation". Mathematical Aspects of Computerized Tomography. G. T. Herman and F. Natterer, Springer Berlin Heidelberg. 8 : 252-269.

International Search Report translation, PCT/JP2014/002571, Nov. 20, 2014, 1 page.

* cited by examiner

X-RAY CT IMAGE PROCESSING METHOD, X-RAY CT IMAGE PROCESSING PROGRAM, AND X-RAY CT IMAGE DEVICE

TECHNICAL FIELD

This invention relates to an X-ray CT (Computed Tomography) image processing method, an X-ray CT image processing program, and a X-ray CT image device.

BACKGROUND ART

The X-ray CT (Computed Tomography) is a technology that conducts imaging of an observation object interior as a distribution of X-ray absorption coefficients based on projection data obtained by irradiating X-rays on observation objects.

Generally, the X-ray CT is configured for an X-ray tube and an X-ray detector to be disposed opposite to each other and a turn table is disposed in between. The rotation axis of this turn table is disposed to be orthogonal against the X-ray axis between the X-ray tube and the X-ray detector. In the X-ray CT device, CT tomographic images are reconstructed by processing the transmitted X-ray data from multiple angles against measuring object. Usually, transmitted X-ray data are gathered with equally spaced rotation by more than 180 degrees.

Heretofore, algorithms for enabling higher precision of X-ray CT reconstruction such as a technology for reconstitution of CT images of similar quality as of the conventional ones at a lower X-ray exposure dose, and another technology for reduction of metal artifacts have been studied. The aforementioned metal artifacts refers to a phenomenon in which an artificial noise is superimposed on reconstruction images as a consequence of reconstruction failure with precision when a measuring object contains a high X-ray absorption material with high density such as a metal. The X-ray CT reconstruction is a method to estimate a distribution of X-ray absorption coefficients of materials internally contained by obtaining the attenuation degree of the X-ray transmitted through a measuring object from projection images obtained under various projection angles. However, high X-ray absorption materials strongly attenuate the X-ray and the transmitted X-ray is lost in observation noises without practically being detected. Especially when the conventional filtered back projection method (FBP: Filtered Back Projection) is utilized, there is a problem that an accurate image reconstruction cannot be performed because of false image generation generally called as metal artifacts in the reconstruction images due to a fact that the FBP method is prone to the influence of noise. Although the FBP method is prone to the influence of noise as mentioned above, the main noise contains a shot noise that conforms to the Poisson distribution, and therefore the signal to noise ratio can be improved by intensifying the irradiation X-ray. By the method mentioned above, the relative noise influence can be made smaller and the image reconstruction accuracy can be improved. However, on the other hand, the radiation exposure dose is increased resulting in generation of probabilistic health risks such as carcinogenesis.

As has been mentioned thus far, the reduction of the X-ray exposure dose and the signal to noise ratio are in the trade-off relationship and a statistical inference method is proposed as a technology to obtain reconstruction images with a signal to noise ratio similar to that of the conventional method at a lower X-ray exposure dose. The statistical inference method can reduce an ill-posedness of estimation in a low dose exposure by utilizing an accurate statistical characteristics of the observation process and the a priori knowledge regarding materials to be imaged. As a result, artifacts included in the reconstruction images can be reduced at the same X-ray intensity and resolution as at the conventional ones.

Currently, the filtered back projection (FBP: Filtered Back Projection), the main stream of the image reconstruction method, PCLIS (Projection Completion Method based on a Linear Interpolation in the Sinogram) and an improved PCLIS do not perform the statistical inference that allows the existence of stochastic observation noise or the probabilistic deviation from the deterministic observation model we assume. The statistical inference method is classified into roughly three methods that are the maximum likelihood estimation method (Maximum Likelihood Estimation: MLE), the maximum a posteriori estimation method and the Bayesian inference method.

The maximum likelihood estimation method (MLE) is a statistical inference method without setting a priori knowledge regarding reconstruction images that represent pixel-wise attenuation coefficients of the object, and the most likely reconstruction image is estimated in terms of the probabilistic observation model that expresses the stochastic observation process. The stochastic observation process expresses a stochastic fluctuation (shot noise) regarding the photon number of the transmitted X-ray and so on.

The MAP estimation method and the Bayesian inference method express a priori knowledge regarding estimation objects in the form of a probability model to be incorporated into estimation. Namely, the MAP estimation method and the Bayesian inference method conduct the estimation considering both the probability model regarding observation and the probability model regarding estimation objects. The estimation object in the case of X-ray CT is an X-ray absorption coefficient. Specifically, the maximum value of the posterior distribution of the X-ray absorption coefficient calculated by the probability model regarding observation and the probability model regarding X-ray absorption coefficients of the object for estimation are set to be the estimated value in the MAP estimation method and the expected value in the posterior distribution of the same X-ray absorption coefficients is set to be the estimated value in the Bayesian inference method. While the MAP estimation method conducts estimation by choosing only one point that provides the maximum value of the posterior distribution, the Bayesian inference method chooses the expected value of the posterior distribution and conducts estimation by an average against the group of the X-ray absorption coefficients that widen the posterior distribution, accordingly. The point that gives the maximum of the posterior distribution can fluctuate sensitively corresponding to an observation noise and accordingly the Bayesian inference method provides more stable and higher precision estimation because the expected value of the posterior distribution is not so much influenced by the observation noise.

Here, the ordinary X-ray CT algorithms mostly estimate a single absorption coefficient for each pixel assuming that the incident X-ray consists of a line spectrum and/or the attenuation coefficient for each pixel does not depend on the spectrum of the incident X-ray. However, the actual X-ray does not consist of a single energy electromagnetic wave but a wave consisting of an energy spectrum continuously distributed toward lower energy starting with a maximum energy determined by the X-ray tube voltage. Also the real materials have energy-dependent attenuation coefficients. Due to these facts, the X-ray of higher energy is transmitted with little absorption when irradiated on a material. However, the attenuation of the lower energy X-rays occurs extensively and a phenomenon called beam hardening in which the X-ray spectral distribution after transmission through a material shifts to a higher energy region occurs.

The phenomena originating in the influence of energy dependence (wavelength dependence) of the X-ray absorption coefficients of a material cannot be correctly expressed by the observation process model wherein the X-ray source consists of a line spectrum and the energy dependence (the wavelength dependence) of X-ray absorption coefficients of a material is not considered, and the incorrect estimation would resultantly induce the beam hardening artifacts. The beam hardening artifacts are generated, in this manner, by an estimation based on the model not considering the energy dependence (the wavelength dependence) of the X-ray absorption coefficient of a material.

In particular, it is known that the striate artifacts called streak artifacts and dark band artifacts wherein X-ray absorption coefficients in the vicinity of high absorption materials are estimated to be lower than the actual value are generated, and this is thought to be remarkably influenced by not considering the influence of the beam hardening.

This phenomenon is explained below.

The X-ray is substantially attenuated when an X-ray is transmitted through high absorption materials such as metals with very high X-ray absorption coefficients. If the character of the high absorption material is expressed by an observation model, it would be presumed that a material with a high X-ray absorption coefficient exists in the vicinity of a high absorption material even with a model not considering the energy dependence (the wavelength dependence) of the X-ray absorption coefficient of the material. However, high energy X-rays transmit easily even when the material has high absorption characteristics. For this reason, some amount of the X-ray is observed even when the majority of photons having main energy corresponding to the X-ray source are absorbed during transmission through a high absorption material.

When high absorption materials exist at multiple separated positions, it is anticipated that the transmitted X-ray, the X-ray that transmits each of those multiple high absorption materials, is attenuated further extensively when materials with high X-ray absorption coefficients are overlapped according to a model that does not consider the energy dependence (the wavelength dependence) of the X-ray absorption coefficient. However, a certain amount of the high energy X-ray is practically observed even when the X-ray is transmitted through multiple high absorption materials. For this reason, a model that does not consider the energy dependence (the wavelength dependence) of the material X-ray absorption coefficient leads to a contradiction against an actual observation result under the assumption that a high absorption material simply exists. When X-ray absorption coefficients are estimated in such a manner that the observation model not considering the energy dependence of the X-ray absorption coefficient of the material contradicts with the actual observation result as little as possible, the dark band artifacts that estimate X-ray absorption coefficients near the high absorption material smaller than the actual values are generated.

A method to separate projection data into a metal region and a non-metal region and to subsequently reconstitute an image in each region, and then to overlap the thus obtained images is known as a method to reduce the metal artifacts. By conducting such a method, the inconsistency of the projection data in the metal region is corrected to reduce the metal artifacts generation. Also, the inventers of the present invention proposed an X-ray CT image processing method capable of reducing the metal artifacts by employing an X-ray CT image processing method that expresses the prior knowledge by a probability distribution characterized by the following parameters defined in the region of each pixel of the reconstruction image, the parameters being a parameter that expresses the existence rate for each tissue of the human body to be imaged, a parameter that expresses the X-ray absorption coefficient for each tissue and a parameter that expresses the spatial continuity extent of each tissue. (Refer to the patent literature 1)

However, the beam hardening artifacts generated by discrepancy between the actual observation process and the observation process not considering energy dependence of the X-ray absorption coefficient of the material has not been eliminated because these methods do not consider energy dependence (wavelength dependence) of the X-ray absorption coefficient.

And, a model considering the energy dependence (wavelength dependence) of the X-ray absorption coefficient as a method to reduce beam hardening artifacts is known. (Non-Patent Literatures 1 to 4) In the model that considers energy dependence (wavelength dependence) of the X-ray absorption coefficient, it is necessary to presume the X-ray absorption coefficient for each X-ray energy level. This leads to generation of ill-posedness as an estimation problem although the estimation problem is based on more accurate physical process. For example, let us consider a problem of estimating X-ray absorption coefficients at two kinds of energy levels by discretizing the X-ray energy for simplification purpose. In such case, the X-ray absorption coefficients to be estimated are increased by twofold compared with that under a conventional assumption even when the observed projection image is the same as the conventional one. Consequently, multiple solutions that do not clearly contradict the actual observation can be generated due to the increase of the degree of freedom for X-ray absorption coefficients. In this case, the estimation result is unstable because the result is sensitively influenced by the subtle observation noise. Thus, a constraint to suppress the degree of freedom of the X-ray absorption coefficient is necessary. Firstly in the non-patent literatures 1 to 3, the energy dependence (wavelength dependence) of the material is expressed by expressing the absorption coefficient depending on the energy at each pixel by weighted sum of the absorption coefficient energy function. The energy dependence (the wavelength dependence) of the X-ray absorption coefficient tends to be attenuated when the energy becomes higher though the extent of this tendency differs according to the material, which is common among each different material. When the X-ray energy is set as an input variable and the function that outputs the X-ray absorption coefficient at that X-ray energy is called the absorption coefficient function, the absorption coefficient function of any material is well expressed by a weighted sum (base function expression) of absorption coefficient functions for a few, typically two, materials because the absorption coefficient functions of different materials are similar to each other.

For example, the material class is determined based on the image obtained by FBP and the image reconstruction is performed based on that knowledge according to the non-patent literature 2. Estimation is performed under the assumption that the X-ray absorption coefficient for each pixel can be expressed by a combination of X-ray absorption coefficients specified for each known material class, as depicted in non-patent literature 4.

In this manner, the method to consider energy dependence (wavelength dependence) of X-ray absorption coefficient has been performed by reducing the degree of freedom of estimation parameters by utilizing a base function expression based on the wavelength dependence of the X-ray absorption coefficient for known material so that the ill-posedness can be suppressed. However, a problem that the constraint imposed is too strong is pointed out. To weaken the constraint, it is desired to represent the constraint in terms of the probabilistic model.

On the other hand, it has become possible, by the advent of DECT (Dual Energy Computed Tomography), to estimate the energy dependence (wavelength dependence) of materials based on the difference of X-ray absorption coefficients by filming at different X-ray tube voltages, from the hardware perspective. Various types of image reconstruction methods employing this DECT are known. (Non-Patent Literature 5 to 8) However, there are problems, one of which, for example, is that the image reconstruction method based on DECT generally requires a higher exposure dose than that of the monochromatic X-ray CT and the estimation accuracy becomes deteriorated when the exposure dose is constrained at that of the monochromatic X-ray CT. Also, the non-patent literature 5 describes a method to perform compensation by a subsequent image processing and thus there is a limit including a possibility of false images to be further generated.

The observation model not considering the energy dependence of the X-ray absorption coefficient of materials assumes that the X-ray consists only of a certain typical wavelength, not of multiple wavelengths. This can be considered to be the simplification of the process where the X-ray of multiple spectra is incident on a detector in a multiple manner. Such a phenomenon that the X-ray of multiple spectra is incident on a detector occurs not only in the spectrum space but also temporally and spatially. Namely, multiple X-rays are incident on the detector within a certain detection time and multiple X-rays are incident on a certain fixed area within the detection area. In the observation process where these projected X-rays are incident on the detector, further in a case where X-rays incident on the detector is represented by a single X-ray, a bias is generated in the estimation of the X-ray absorption coefficient in a similar manner where the beam hardening artifacts are generated when the energy dependence of the X-ray absorption coefficient is not considered. (Non-Patent Literature 9) That is to say, it is desirable to treat the projected X-ray to be incident on the detector as a sum of multiple X-rays assuming multiple beams not a single beam (not ignoring multiplicity of the X-ray) in the observation process.

PRIOR ART

Patent Literature

[Patent literature 1] JP 2011-156302 A

Non-Patent Literature

[Non-patent literature 1] Joseph A. O'Sullivan, and Jasenka Benac, Alternating Minimization Algorithms for Transmission Tomography, IEEE TRANSACTIONS ON MEDICAL IMAGING, VOL. 26, NO. 3 (2007), 283-297

[Non-patent literature 2] Idris A. Elbakri and Jeffrey A. Fessler, Senior Member, IEEE, Statistical Image Reconstruction for Polyenergetic X-Ray Computed Tomography, IEEE TRANSACTIONS ON MEDICAL IMAGING, VOL. 21, NO. 2 (2002), 89-99

[Non-patent literature 3] Joseph A. O'Sullivan, Bruce R. Whiting, Donald L. Snyder, and Orville A. Earl, Image Reconstruction from Data Acquired With an X-Ray Computerized Tomographic System Having Energy-Integrating Detectors

[Non-patent literature 4] Chye Hwang Yan, Robert T. Whalen, Gary S. Beaupre, Shin Y. Yen, and Sandy Napel, Reconstruction Algorithm for Polychromatic CT Imaging: Application to Beam Hardening Correction, IEEE TRANSACTIONS ON MEDICAL IMAGING, VOL. 19, NO. 1, (2000)

[Non-patent literature 5] A J Coleman and M Sinclair, A beam-hardening correction using dual-energy computed tomography, Phys. Med. Biol., 1985, Vol 30, No. 11, (1985), 1251-1256

[Non-patent literature 6] Jeffrey A. Fessler, Idris Elbakri, Predrag Sukovic, Neal H. Clinthorne, Maximum-likelihood dualenergy tomographic image reconstruction, Medical Imaging 2002: Image Processing, Milan Sonka, J. Michael Fitzpatrick, 38 Editors, Proceedings of SPIE Vol. 4684 (2002), 38-49

[Non-patent literature 7] Joonki Noh, Jeffrey A. Fessler Paul E. Kinahan, Statistical Sinogram Restoration in Dual-Energy CT for PET Attenuation Correction, IEEE Trans Med Imaging, (2009) 1688-1702

[Non-patent literature 8] Y. Yamazaki, N. Toda, Dual-Energy X-ray CT noise reduction algorithm under low exposure environment, IEICE Technical Report MBE2008-113, (2009), 101-106

[Non-patent literature 9] Ruhrnschopf, E. P., G. Schwierz, et al. (1981). Nonlinearity and Inhomogenity Effects in Computerized Tomography Due to the Exponential Attenuation of Radiation. Mathematical Aspects of Computerized Tomography. G. T. Herman and F. Natterer, Springer Berlin Heidelberg. 8:252-269

OUTLINE OF THE INVENTION

Problems to be Solved by the Invention

As was described above, the hard X-rays with short wavelengths and higher energies transmit the material more easily than the soft X-rays with longer wavelengths and lower energies, and accordingly the spectral distribution of the X-ray incident on the material after transmitting the material becomes the one with the peak of the power spectra shifted toward the hard X-ray side with the attenuation of soft X-rays, which is a phenomenon called beam hardening.

This problem is solved, ideally, by employing the spectral analysis on the transmitted X-ray, then measuring the X-ray at each of spectral intensity, and finally estimating the X-ray absorption coefficient at each spectrum based on the measurement. However, there are problems that presumption accuracy deteriorates because the signal to noise ratio deteriorates due to the decrease of each signal by extracting certain spectral intensity. For this reason, there has been a demand that the beam hardening artifacts are eliminated by information processing algorithms.

Among various information algorithms proposed for eliminating the beam hardening artifacts, there is a method to consider the wavelength dependence of X-ray absorption coefficients of materials and also there is a technology that reduces the degree of freedom for parameter presumption by specifically employing a base function expression utilizing the X-ray absorption coefficient wavelength dependence of the tissue. (Refer to Non-Patent Literatures 1, 2)

However, because the textural class, in which the textural type is expressed by discrete variables, is presumed by determinism as depicted in non-patent literatures 1 and 2, there are such problems that the texture not expressed by a known textural class is not properly expressed or that the presumed textual class is wrong, resulting in the markedly diverged solution, in such cases where the assumed texture class is not proper or where the texture class is wrongly presumed.

Also, there is a problem that the presumption of the texture class tends to become unstable due to a fact that the cancellation of ill-posedness is not enough because constraint was not posed regarding the texture class to be presumed.

In particular, as depicted in the non-patent literature 1, the X-ray absorption coefficient ratio among wavelengths can be varied and the different texture classes are weighted. There is a possibility that an X-ray absorption coefficient that cannot be expressed appears when the texture class number is small and the constraint becomes meaningless generating the ill-posedness when the texture class number is large.

Therefore, in comparison to the image reconstruction using the conventional technologies, the present invention is aimed to present an X-ray CT image processing method, an X-ray CT image processing program and an X-ray CT image processing equipment furnished with said program, by expressing the X-ray absorption coefficient "stochastically" through the material class which is a discrete variable for expressing the material class and suppressing the ill-posedness by stochastically restraining the material class, on the other hand, enabling more flexible expression of the X-ray absorption coefficient by estimating which material class each pixel belongs to stochastically not deterministically, thus providing capability for acquiring reconstruction images comparable to the conventional ones, by a lower X-ray exposure dose and consequently capable of reducing the artifacts. Here, the material class is not necessarily an organism tissue and the material class is used with the inclusion of a tissue class, accordingly.

Also, it is necessary to grasp the X-ray incident on the detector as a sum of multiple beams assuming a plurality of X-rays, not a single X-ray beam. As was mentioned above, a bias generation occurs by having the incident beam represented by a single beam ignoring this X-ray multiplicity in terms of the energy (wave length).

Therefore, the present invention aims to present an X-ray CT image processing method, an X-ray CT image processing program and an X-ray CT image processing equipment furnished with said processing program, capable of reducing the bias caused by the single beam representation, with a statistical inference of the probability distribution regarding the observation of the projected X-ray incident on the detector in the multiple mode.

Means to Solve the Objects

In view of the above mentioned circumstance, the X-ray CT image processing method according to the present invention performs statistical inference by setting a probability distribution regarding the X-ray projection image observation.

The above mentioned probability distribution expresses the observation process of the multiple-X-ray sum incident on the detector in the multiple mode of the X-ray projected. Here, the multiple-X-ray sum means that the signal detected at the X-ray detector is modeled as the consequence of not a single X-ray incident to a point, but multiple X-rays incident to the spatially different points on the detector surface, and/or not an instantaneous X-ray incident to the detector at certain time point, but multiple X-rays incident to the detector at different time points during exposure time, and/or not an X-ray whose spectrum is line spectrum, but an X-ray whose spectrum is continuously distributed in different energy, in other words, that the multiple X-rays with different spatial positions, arrival time and the wavelengths are incident on the detector and that the weighted sum of those multiple X-rays is observed by the detector.

And, under the observation process that expresses the multiple-X-ray sum and the prior distribution regarding the X-ray absorption coefficient which is characterized by material class, the statistical estimates of the X-ray absorption coefficient and the material class are given as the expectation value of the posterior distribution regarding the X-ray absorption coefficient and the material class.

Here, the observation process expressed by the multiple-X-ray sum relaxation has the following characteristics that are (a) and (b) as described below.

(a) The X-ray absorption coefficients dependent on the wavelength at each pixel is expressed by the product of the X-ray absorption density of each pixel and the X-ray absorption coefficient ratio among X-ray absorption wavelengths predetermined for each material. The estimation of the X-ray absorption coefficient in the case where the wavelength dependence of the X-ray absorption coefficient is not considered becomes equivalent to estimating only the X-ray absorption coefficient density considering that only one supposed X-ray wavelength region is assumed to exist for the X-ray absorption coefficient possessing the wavelength dependence. For this reason, the expression of the product of the X-ray absorption coefficient density of each pixel of the X-ray absorption coefficient possessing the wavelength dependence and the X-ray absorption coefficient ratio among X-ray absorption wavelengths predetermined for each material becomes an extension of the expression for the X-ray absorption coefficient not considering the wavelength dependence of the X-ray absorption coefficient.

(b) In a case of the multiple-X-ray sum considering a sum regarding X-ray wavelength, a X-ray absorption coefficient having wavelength dependence of each pixel is expressed as a product of an X-ray absorption coefficient density of each pixel not depending on wavelengths and an X-ray absorption coefficient ratio among X-ray wavelengths specified for each the material not depending on the pixel. The X-ray absorption coefficient is expressed using a parameter for expressing an X-ray absorption coefficient ratio among X-ray wavelengths determined for each material. And a prior distribution of an X-ray absorption coefficient having a wavelength dependence of each pixel is expressed by a conditional prior distribution against the X-ray absorption coefficient density of each pixel under a condition of material and a prior distribution against material.

Also, the prior distribution regarding the X-ray absorption coefficient that expresses the tendency of the X-ray absorption coefficients shown by the imaging object is determined by a variable called a material class. The material class is a variable defined by each pixel inside the imaging target that shows which material constitutes the inside of the imaging target. The material class constrains the flexibility of the wavelength dependent X-ray absorption coefficient stochastically by constraining the easiness of the material class generation and the extent of spatial smoothness of each material class stochastically.

Also, in a case where a probability distribution showing the value the X-ray absorption coefficient density tends to be settled at is expressed by the sum of 2 gamma distributions when the material class is fixed, the degree of freedom of the X-ray absorption coefficient dependent on the wavelength is stochastically constrained by adding a stochastic constraint which is a likelihood of a certain material class and subclass combination generation for the combination of the material class and the subclass, and also the extent of spatial smoothness for each combination of the material class and the subclass after introducing a subclass variable of the material class, for expressing which one of each gamma distributions the probability distribution belongs to.

According to the X-ray CT image processing method of the present invention, to eliminate the artifacts generated by ignoring the observation process of the multiple-X-ray sum including the beam hardening artifacts, the X-ray CT image processing is performed by setting a probability distribution considering the observation process of multi X-ray summation such as the wavelength dependence of the X-ray absorption coefficient of the material. Here, when the wavelength dependence of the material X-ray absorption coefficient is considered, a reliable solution is not obtained due to ill-posedness of the problem when the X-ray absorption coefficient for each wavelength is all estimated as unknown variables, and a prior distribution for expressing the fact that a number of known materials possess X-ray absorption coefficients with a specific wavelength dependence is to be utilized to obtain a more reliable solution by changing the task to an easier estimation that is to estimate which material class out of the known material classes constitutes each pixel of the reconstruction image. Namely, instead of estimating the X-ray absorption coefficients as positive real variables for each wavelength, the X-ray absorption coefficient density which is a positive real variable independent of the wavelength and the material class which is a discrete variable are estimated. The material class of each pixel is treated as hidden state variables, namely the variables of the material class are treated as stochastic variables.

The degree of freedom of the X-ray absorption coefficient dependent on the wavelength is arranged to be stochastically constrained by imposing a stochastic constraint of spatial smoothness against this material class being a hidden state variable. Moreover, as a deduction of probability distribution with hidden variables, a stable and high precision estimation (a stable estimation not responding to observation noises too sensitively with guaranteed convergence) based on the approximate execution of the Bayesian inference is conducted. Also, according to the Bayesian inference in the present invention, the posterior distribution is approximated by employing a test distribution capable of good approximation, upon estimation of both the posterior distribution regarding the X-ray absorption coefficient and the material class to which the region of each pixel of the reconstruction image belong. The X-ray absorption coefficient can be expressed in a more flexible and delicate manner compared with the situation where the material class is selected deterministically, because the attachment probability of the material class at each pixel and the X-ray absorption coefficient density of each pixel can be stochastically expressed by the Bayesian inference.

According to the X-ray CT image processing method in this invention, a flexible expression by the weighted sum becomes possible even for the material not expressed by the known material class by operating the variable of the material class as a probability variable. Also, according to the X-ray CT image processing method in this invention, the ill-posedness can be suppressed by imposing the constraint such as spatial smoothness to the material class as a prior knowledge. Also, according to the X-ray CT image processing method in this invention, the convergence is guaranteed and the instability (overfitting) of estimation can be restrained by conducting the approximated Bayesian inference. Namely, the estimation more precise to the physical process with high accuracy and stability can be performed by employing the X-ray CT image processing method in this invention.

In this invention, the expression "the material class" is used by the meaning that includes a textural class. The material class is expressed by discrete variables. The abundance ratio (density) of the material class is a parameter of a non-negative scalar indicating the variety of material class (ordinary cells such as muscle, soft cells such as fat, bone, metal and so on) and the distribution rate thereof.

The parameter for expressing the X-ray absorption coefficient ratio fixed among wavelengths for each material class constrains the degree of freedom of the X-ray absorption coefficient dependent on the wavelength, under an assumption that the absorption coefficient rates among wavelengths are fixed for the X-ray absorption coefficients stochastically expressed, which is applied to the stochastic distribution of the prior knowledge.

Also, the parameter that expresses the spatial continuation extent for the material class constrains the degree of freedom of the X-ray absorption coefficient dependent on the wavelength by applying the extent for the material class to be spatially continuous to the probability distribution of the prior knowledge because the constraint that the extent of spatial continuation is high in such a case, for example, that the material class of air provides pixels easily connected (other structures do not enter into air) can be imposed.

According to the X-ray CT image processing method described above, the image reconstruction and the material inference are conducted by using the Bayesian inference based on the expected value of the posterior probability by expressing the distribution information in the form of a probability distribution such as, the kind of material class (ordinary cells such as muscle, soft cells such as fat, bone, metal and so on) distributed, the distribution rate thereof, the extent of the X-ray absorption coefficient for each material class and the extent of spatially continued distribution for each material class.

Note that the prior knowledge regarding the material class can employ a fixed average parameter. However, it is possible to further improve the image reconstruction and the material cluster inference accuracy by adequately changing the parameter according to individual differences such as physique, medical history, the distinction of sex, age and the imaging site.

Suppose a case in which a sum regarding X-ray wavelengths is included in the multiple-X-ray sum in the X-ray CT image processing method according to the present invention.

In this case, the kind of X-ray absorption coefficient which is likely to be generated is stochastically limited by characterizing the prior distribution for the X-ray absorption coefficient dependent on the wavelength of each pixel through parameters expressing the X-ray absorption coefficient distribution for each material class and each X-ray wavelength.

Other viewpoint points out that, in a case where a sum regarding the X-ray wavelength is included in the multiple-X-ray sum according to the X-ray CT image processing method of the present invention, the X-ray absorption coefficient dependent on each pixel is expressed by the product of the X-ray absorption coefficient density of each pixel not dependent on the material class and the X-ray absorption coefficient ratio among the X-ray wavelengths specified for each material class.

And the X-ray absorption coefficient with wavelength dependence of each pixel is characterized by a parameter expressing the X-ray absorption coefficient ratio among X-ray wavelengths determined for each material class.

And, the prior distribution of the X-ray absorption coefficient possessing the wavelength dependence of each pixel is expressed by a conditional prior distribution regarding the X-ray absorption coefficient density of each pixel with a material class as a condition and the prior condition concerning the material class.

Namely, when the X-ray absorption coefficient is expressed by the product of the X-ray absorption coefficient density of each pixel and the material class, a prior distribution of X-ray absorption coefficients is uniquely determined by a prior distribution for the X-ray absorption coefficient density of each pixel and a prior distribution for a material class.

Here, in the X-ray CT image processing method of the present invention, the X-ray absorption coefficient density distribution specified for each material class mentioned above is expressed by the mixed gamma distribution. And the material class is expressed by the Boltzmann distribution characterized by a parameter for expressing the material class occurrence extent and a parameter for expressing the material class spatial continuity extent.

This is one example about the expression for the prior distribution of the X-ray absorption coefficient.

By assuming a mixed gamma distribution against the X-ray absorption coefficient density with the material class as a condition and also assuming a Boltzmann distribution against the material class variables, the prior distribution of the X-ray absorption coefficient is arranged to be determined.

The reason that the distribution of the X-ray absorption coefficient density set for each material class can be expressed by the (mixed) gamma distribution is based on noticing that the distribution shape can express the single peak distribution and the stochastic variable is guaranteed to become always positive. Also, the reason that the signal distribution observed at the detector in the observation process of the multiple-X-ray sum incident on the detector in multiple mode of the projected X-ray can be expressed by a Gaussian distribution is a fact that the distribution of the observed signal shows a value off the ideal value due to noises such as optical scattering and quantization noise and these noises are assumed to be well expressed by the Gaussian distribution considering that the calculation is easy even when the projected X-ray is multiple.

Also, the reason that the material class can be expressed by the Boltzmann distribution which is characterized by a parameter for expressing the extent for appearance of said material class and by a parameter for expressing the extent for said material class to be spatially continuous is due to noticing that the same organism tends to be spatially gathered (coordination of gathering easiness by structure) and the easiness of expressing the rate of each structure assumed to be the standard.

Also, in the X-ray CT image processing method according to the present invention, the Bayesian inference estimates the material class, the X-ray absorption coefficient density, the subclass variables and the posterior distributions thereof. Here, the subclass variable is a discrete variable for specifying which of the two gamma distributions the material class belongs to in a case where the probability distribution is expressed by the sum of two gamma distributions showing the kind of X-ray absorption coefficient density the material class tends to take when the material class is fixed.

It is considered that the prior distribution of the X-ray absorption coefficient under a condition that the material class is given tends to show a specific value (an average for example). However, because it is expected that the prior distribution of the X-ray absorption coefficient does not necessarily become a probability distribution symmetrical around the average value and the kurtosis of the probability distribution can be expected to be large or small, the prior distribution is expressed by a mixed probability distribution which is a weighted sum of two probability distributions so that such a complex prior distribution can be expressed. Further, it is assumed that the mixed probability distribution can be expressed by the mixed probability distribution of the gamma distribution because the X-ray absorption coefficient takes only a plus value. The subclass variable of the material class is a binary variable taking only 0 or 1, conveniently introduced for designating which probability distribution out of two mixed probability distributions the prior distribution belongs to.

The X-ray CT image processing equipment of the present invention, being an X-ray CT image processing equipment for performing statistical inference by setting a probability distribution regarding observation of X-ray projection images, comprising input means for inputting measurement conditions including X-ray projection images and at least an X-ray intensity and estimation means for estimating an X-ray absorption coefficient and a material class by the Bayesian inference based on an expected value of posterior distribution regarding the X-ray absorption coefficient and the material class under a probability distribution regarding observation, a prior distribution regarding an X-ray absorption coefficient expressed through a variable for expressing which material exists at each pixel of a reconstruction image called a material class and a prior distribution regarding material class. Here, the probability distribution regarding observation is set as a probability distribution expressing what kind of projection image is easily obtainable through an observation process of multiple-X-ray sum incident on the detector resulting from the projected X-ray in multiple. Also, multiple-X-ray sum means that the X-ray detection surface at the detector possesses a predetermined expanse not a point spatially, the X-ray detection time possesses a predetermined time width not a an instant, the X-ray spectral distribution possesses a predetermined width not a line spectrum, multiple X-rays with different spatial positions and the directions are incident on the detector and the weighted sum of these multiple X-rays are observed by the detector.

According to the X-ray CT image processing equipment mentioned above, by dealing with the material class variables as probability variables using parameters for expressing the abundance (density) of the material class, an approximation expression becomes possible for the material deviated from the predetermined material class by the expression of weighted sum of the predetermined material class. Also, the ill-posedness can be restrained by imposing constraint of spatial smoothness class as a probability distribution to the material class by using a parameter that expresses the spatial continuation extent for the material class.

Further, when this invention is viewed from another point, this invention concerns an X-ray CT image processing program for conducting stochastic estimation by assuming a probability distribution regarding the X-ray absorption coefficient and letting a computer operate the following 1) to 2) steps.

1) A step for inputting measurement conditions including X-ray projection images and at least an X-ray intensity
2) A step for estimating an X-ray absorption coefficient and a material by the expected value of the posterior distribution regarding the X-ray absorption coefficient and the material under the prior distribution regarding the X-ray absorption coefficient having parameters regarding the material Here, the probability distribution mentioned above is expressed as an observation process of the sum of the multi X-rays incident on the detector in multiple of the projected X-rays and the multiple-X-ray sum means that the X-ray detection surface at the detector possesses a predetermined expanse not a point spatially, the X-ray detection time possesses a predetermined time width not a an instant, the X-ray spectral distribution possesses a predetermined width not a line spectrum, multiple X-rays with different spatial positions and the directions are incident on the detector and the weighted sum of these multiple X-rays are observed by the detector.

According to the X-ray CT image processing program mentioned above, even for materials not expressed by the known materials, a flexible expression by weighted sum of those materials becomes possible by handling the material variable as a probability variable using a parameter for expressing the abundance (density) of the material. Also, ill-posedness can be restrained by imposing the constraint of the spatial smoothness as the probability distribution against the material with a parameter for expressing the spatial continuity of the material.

Also, this invention can provide an X-ray CT image processing equipment furnished with the above mentioned X-ray CT image processing program.

Effects of the Invention

According to the present invention, in comparison with the image reconstruction using the conventional technologies, effects such as a more flexible expression by expressing the X-ray absorption efficient stochastically, availability of the reconstruction images with the same quality as the one conventionally obtained by a lower X-ray exposure dose and reduction of hardening artifacts are brought about.

Also, according to the present invention, there is an effect to reduce the bias due to representation by a single beam, based on statistical inference after setting the probability distribution regarding the observation process of the multiple-X-ray sum for the projected X-ray to be incident on the detector in a multiple mode.

BEST MODE FOR CARRYING OUT THE INVENTION

Figure 1:
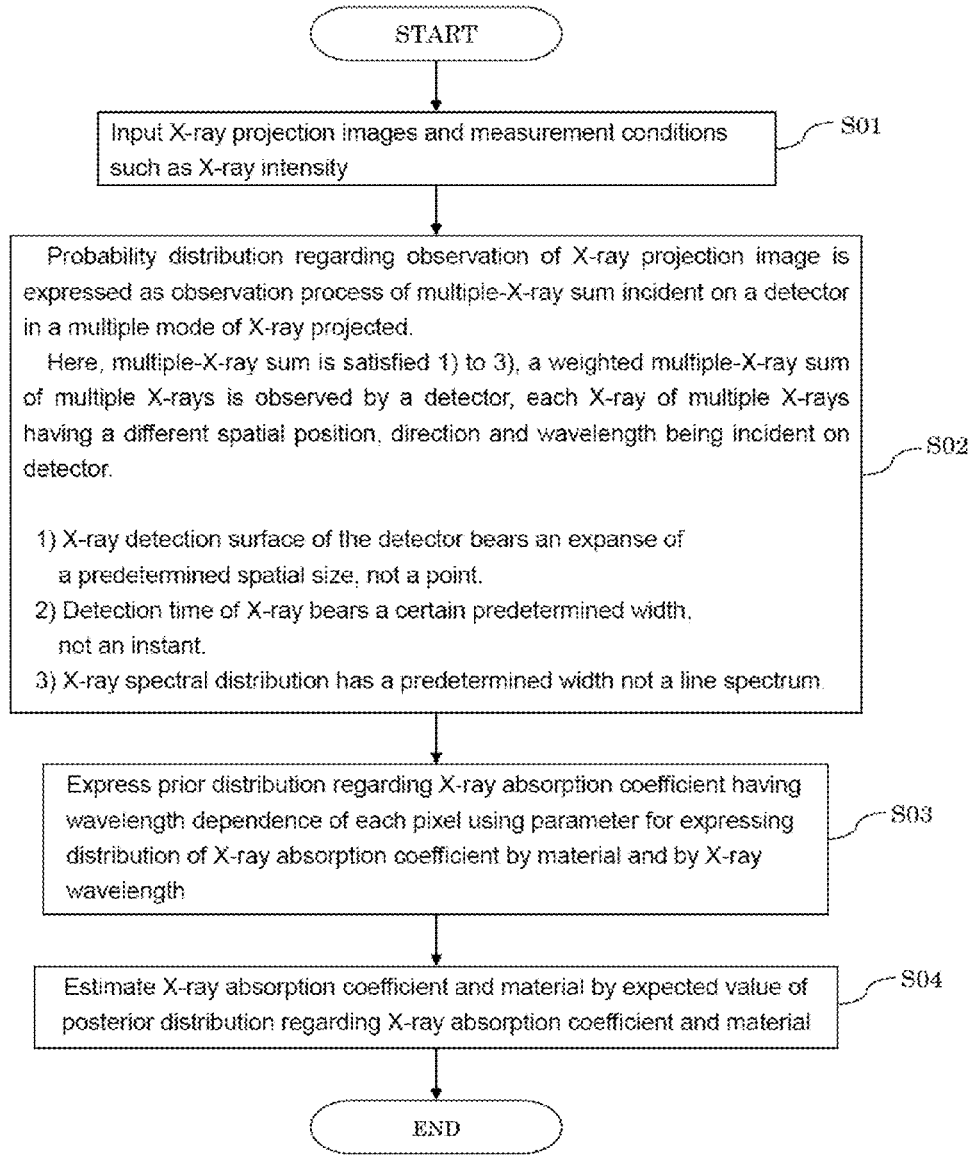
FIG. 1 A process flow of the X-lay CT image processing method of the present invention
FIG. 2 An explanatory drawing of the X-ray CT
FIG. 3 An explanatory drawing of the update
FIG. 4 A probability distribution drawing of the metal and bone X-ray absorption coefficients
FIG. 5 A figure showing the image reconstruction at the computer experiment of embodiment 1
FIG. 6 A figure showing the image reconstruction at the computer experiment of embodiment 2
FIG. 7 An explanatory drawing of the projection geometry for the parallel beam
FIG. 8 An explanatory drawing of the projection and the encoding for the parallel beam
FIG. 9 An explanatory drawing of the projection geometry under rotation

Embodiments of the present invention will be described in detail below with reference to the drawings. The present invention is not limited to the following embodiment and examples of shown in the figure, and the present invention can be variously changed in design.

In the X-ray CT image processing method and the X-ray CT image processing program according to the present invention, the image reconstruction is performed using a statistical inference along with the setting of the prior distribution regarding the X-ray absorption coefficient. Especially, the beam hardening artifacts are disbanded by the estimation of the energy dependent (wavelength dependent) X-ray absorption coefficient based on a statistics model considering the energy distribution (the wavelength distribution).

To address the ill-posedness induced by the increase of variables to be estimated, it is necessary to solve the problem by imposing some kind of constraint on the solution by using some proper prior knowledge. In the present invention, by using a basis function expression, the basis thereof being assumed to be an X-ray absorption coefficient dependent on energy (dependent on wavelength) of a known material and being also assumed to be given by a product of a discrete variable for expressing the material class the weight belongs to and a continuous variable of a non-negative scalar for expressing an X-ray absorption coefficient density, a constraint is imposed on the solution by imposing a prior distribution of X-ray absorption coefficients under a condition of a material class and the prior distribution of the material class.

Also, according to the present invention, in the case of a reconstruction image targeting human tissue, the human tissue consists of limited materials such as fat, muscle, bone, and because a rough distribution of the X-ray absorption coefficient of each material is known in advance, such knowledge as mentioned thus far is expressed as a prior distribution to be utilized for estimation. For this estimation, it is necessary to estimate the material class each pixel belongs to, however, based on the fact that each material possesses spatial continuity and a situation in which the percentage for each material to occupy the human body can be assumed, ill-posedness can be restrained by introducing the prior knowledge such as a spatial smoothness constraint and an occupancy ratio to the discrete variable for expressing the material class.

The observation process of a projected X-ray expresses the observation process of multiple-X-ray sum of the projected X-ray incident on a detector in a multiple mode, and also expresses that multiple X-rays of different wavelengths are incident on a detector, the X-rays having wavelength regions (spectral distributions) of a finite width.

The probability distribution regarding the reconstruction images characterizes the way for expressing the tendency of the X-ray absorption coefficient value to be settled at, in the region of each pixel of the reconstruction images, and it is expressed by a Boltzmann distribution consisting of a mixed gamma distribution expressing the tendency of the X-ray absorption coefficient density for the combination of each material class and each subclass variable to take, a parameter expressing the extent for the combination of each material class and each subclass variable to emerge and a parameter expressing the extent for the combination of each material class and each subclass variable to be spatially continuous.

And the statistical inference by the expectation estimation of the posterior distribution regarding the X-ray absorption coefficient and the material class is performed. At image reconstruction, it is necessary to find this posterior distribution. However, it is difficult to execute the calculation analytically because the sum calculation regarding the high order hidden discrete state variable which is a material class defined at each pixel is included. Therefore, in this invention, this calculation difficulty is overcome by applying an approximation method. (Refer to a flowchart in FIG. 1)

(Formalization of the Problem)

As in the X-ray CT image, T projection data projected from various directions are to be expressed by $D=\{Y^{(1)}, *, Y^{(T)}\}$. Each data $Y^{(t)}$ is a set of data detected by the detector through the t-th projection and becomes $Y^{(t)}=\{y_1^{(t)}, *, y_I^{(t)}\}$. Note that T is a projection number, I a number of the detector and $y_i^{(t)}$ is the photon number detected at the i-th detector. And the equation (1) below is formed, because the X-ray is attenuated exponentially when transmitted through a material.

[Equation 1]

$$\hat{y}_i^{(t)} = b_i^{(t)} \exp\left\{-\sum_{j=1}^{J} l_{ij}^{(t)} x_j\right\} \qquad (1)$$

Figure 2:
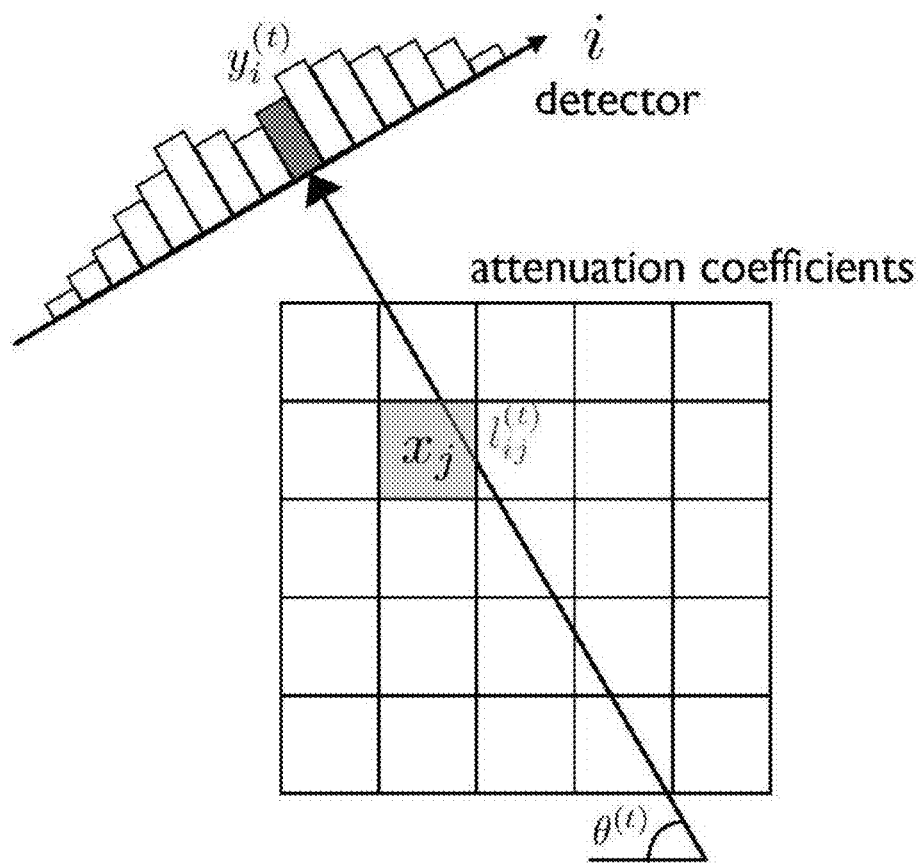

Here, $x_j$ is an X-ray absorption coefficient of the j-th pixel in the J-dimensional vector $x=\{X_1, ***, X_J\}$ obtained by a raster scan of the X-ray absorption coefficient of the imaging object on an observation object. $b_i^{(t)}$ expresses the photon number emitted from the X-ray source (the number of photons observable when no object is placed). Also, $l_{ij}^{(t)}$ corresponds to the intersection distance between the projection line detected by the i-th detector when projected from the angle $\theta^{(t)}$ and the i-th pixel, and $l_{ij}^{(t)} x_j$ expresses the effective X-ray absorption coefficient of the j-th picture region against the X-ray incident on the i-th detector for the t-th projection. (Refer to FIG. 2)

Here, the expression for discretization of the X-ray energy spectrum into E is considered. If the photon number of the X-ray belonging to energy e (e=1, ***, E) within the incident X-ray is assumed to be N $e^{(t)}$, the average photon number observed after transmitting a material can be expressed by the equation (2) below.

Note that $x_{je}$ is the X-ray absorption coefficient of the j-th pixel against the X-ray of energy e.

[Equation 2] (2)

$$\hat{y}_i^{(t)} = \sum_{e=1}^{E} N_e^{(t)} \exp\left\{-\sum_{j=1}^{J} l_{ij}^{(t)} x_{je}\right\}$$

(Energy Dependence of the X-Ray Absorption Coefficient)

The ill-posedness is generated if the X-ray absorption coefficient $x_{je}$ of j-th pixel at an energy e is freely determined by each energy and each pixel. Practically, every material has a character, roughly common among materials, that the X-ray absorption coefficient becomes smaller with the increase of energy. Namely, the ratio of X-ray absorption coefficients of different energy shows a specific tendency.

Therefore, the X-ray absorption coefficient is expressed under a constrained way by introducing a material class for classifying materials.

Assume that the material for observation is classified into C kinds of material classes. Here, the material class of the j-th pixel is expressed by using a variable $z_j$. Note that Z is expressed as $Z_j=\{Z_{j1}, ***, Z_{jC}\}$. Each element $z_{jC}$ is a binary variable taking either 0 or 1, taking 1 when the j-th pixel belongs to the material class C and taking 0 for other cases. As a variable for expressing a ratio of X-ray absorption coefficient among energies uniquely determined depending on this material class, a rate of variability $r_{cs}$ (>0) is defined. Note that the rate of variability $r_{cs}$ is assumed to be normalized as $r_{cs}=1$ when e=1. The X-ray absorption coefficient of the j-th pixel under the condition e=1, is expressed by $X_j(0>)$. By using the expression above, the absorption coefficient $x_{js}$ can be expressed as shown in the equation (3) below.

[Equation 3]

$$x_{je} = \sum_{c=1}^{C} r_{ce} z_{jc} x_j \qquad (3)$$

When the equation (3) above is used, the variables to be estimated at each pixel become only two, the one is an $x_j$ scalar continuous variable and another is a discrete variable z taking one of the values of C kinds.

(Regarding the Observation Model)

The ideal value of the photons observed at each detector follows the equation (1) mentioned above. However practically, it is known that the observation value is off the ideal value due to noises such as photon scattering and quantization noise. If these noises are assumed to be well expressed by the Gaussian distribution, the observation data at each detector can be expressed by the equation (4) below. Note that $X=\{x_1, *, X_j\}$, and $Z=\{z, *, z_j\}$.

Also, if the observation is assumed to be independent for each detector and for each projection, a set D of the projection data (observation data) can be expressed by the equation (5) below. Note that T is the number of projection and I is the number of detector. Here, $\sigma$ that represents a standard deviation of the Gaussian distribution can be treated as a function to be dependent on the observation $y_i^{(t)}$ as shown by the equation (4) below, considering the nature of the shot noise.

[Equation 4]

$$p(y_i^{(t)} | X, Z) = \frac{1}{\sqrt{2\pi\sigma}} \exp\left\{-\frac{(\hat{y}_i^{(t)} - y_i^{(t)})^2}{2\sigma^2}\right\} \qquad (4)$$

$$\sigma = \sqrt{y_i^{(t)} + v}$$

(Note v is a constant)

[Equation 5]

$$p(D | X, Z) = \prod_{t=1}^{T} \prod_{i=1}^{I} p(y_i^{(t)} | X, Z) \qquad (5)$$

$$= \prod_{t=1}^{T} \prod_{i=1}^{I} \frac{1}{\sqrt{2\pi\sigma}} \exp\left\{-\frac{(\hat{y}_i^{(t)} - y_i^{(t)})^2}{2\sigma^2}\right\}$$

(Regarding the Prior Distribution)

With regard to the prior distribution, the prior knowledge regarding the X-ray absorption coefficient for each material class of the observation object is expressed. If the X-ray absorption coefficient $x_j$ at the pixel j is assumed to be determined depending only on the material class $z_{jc}$ at the pixel j, the prior distribution p (X/Z) can be expressed by the equation (6) below.

[Equation 6]

$$p(X \mid Z) = \prod_{j=1}^{J} p(x_j \mid z_j) \quad (6)$$

When the material class $Z_{jc}$ is given, the expectation for the X-ray absorption coefficient $x_j$ tends to take some specific value. Here, the prior distribution p $(s_j/z_j)$ can be expressed according to the equation (7) below as a mixture distribution of 2 distributions so that the asymmetry of the distribution and various different kurtosis can be expressed. Note that the variable b is a binary variable. Also the vector B is defined as B={$b_1$, ***, $b_J$}.

[Equation 7]

$$p(x_j \mid z_j) = \sum_{b_j} p(x_j \mid z_j, b_j) p(b_j) \quad (7)$$

$b_j = [b_{j1}, b_{j2}] \in \{[0,1],[1,0]\}$

When the material class $z_{jc}$ and the variable $b_{jc}$ for each pixel are given, the X-ray absorption coefficient $x_j$ can be expressed, under an assumption that it follows the gamma distribution, by the equation (8) below. Note that $u_{cd}$, and $v_{cd}$ are parameters of gamma distribution, $u_{cd}/v_{cd}$ being an average and $u_{cd}/v^2_{cd}$ being dispersion. These parameters are set by empirical knowledge regarding the material class.

[Equation 8]

$$p(x_j \mid z_j, b_j) = \prod_{c=1}^{C} \prod_{d=1}^{2} \left[ \frac{1}{\Gamma(u_{cd})} v_{cd}^{u_{cd}} x_j^{u_{cd}-1} e^{-v_{cd}x_j} \right]^{z_{jc}b_{jd}} \quad (8)$$

Also, in the prior distribution, the variable $Z_{jc}$ satisfying the equation (9) below is a binary variable taking 0 or 1. Employment of the gamma distribution can express that the X-ray absorption coefficient does not become a negative value.

[Equation 9]

$$\Sigma_c z_{jc} = 1 \quad (9)$$

Here, regarding the prior distribution of the variables Z and B, independency among variables is not assumed and follow the gamma distribution as is expressed by the following equation (10). Note that A is a normalization term and the energy H (Z, B) is defined by the following equation (11). In the formula (11) below, 4 pixels neighboring lengthwise and breadthwise are considered to be the vicinity of a 2 dimensional plane and each $G_{cd}^{self}$ and $G_{cd}^{inter}$ is a non-negative constant.

[Equation 10]

$$p(Z, B) = \frac{1}{A} \exp\{-H(Z, B)\} \quad (10)$$

[Equation 10]

$$p(Z, B) = \frac{1}{A} \exp\{-H(Z, B)\} \quad (10)$$

[Equation 11]

$$H(Z, B) = \quad (11)$$

$$-\sum_{j=1}^{J} \sum_{c=1}^{C} \sum_{d=1}^{2} G_{cd}^{self} z_{jc} b_{jd} - \sum_{j=1}^{J} \sum_{s \in \eta(j)} \sum_{c=1}^{C} \sum_{d=1}^{2} \sum_{k=1}^{2} G_{cd}^{inter} z_{jc} z_{sc} b_{jd} b_{sk}$$

η(j): A set of neighboring pixels for the j'th pixel (About Posterior Distribution)

The reconstruction of the X-ray CT image according to the present invention, an X-ray absorption coefficient X, a material class Z and a variable B are estimated as a posterior distribution. The X-ray absorption coefficient X, the posterior distribution p (X, Z, B/D) can be expressed by the equation (12) below by the Bayesian theorem.

[Equation 12]

$$p(X,Z,B|D) \propto p(D|X,Z)p(X|Z,B)p(Z,B) \quad (12)$$

(Bayesian Inference)

Although the expected value of the posterior distribution p (X, Z, B/D) expressed by the equation (12) above becomes necessary according to the Bayesian inference, the posterior p (X, Z, B/D) is approximated by the test distribution q (X, Z, B) in view of the difficulty of estimating this posterior distribution p (X, Z, B/D) analytically. The test distribution q (X, Z, B) can be selected arbitrarily as long as it can minimize or approximately minimize the equation (12) mentioned above. And the tolerance of the test distribution q (X, Z, B) and the posterior distribution p (X, Z, B/D) is evaluated by the KL (Kullback-Leibler) distance to compute the test distribution q (X, Z, B) that minimize the KL distance. Here, the KL distance can be expressed by the equation (13) below.

Note that $<^*>_{q(X, Z, B)}$ is an operator for performing integral computation regarding the distribution q (X, Z, B). The KL distance is always non-negative and becomes 0 (zero) only when q=p. $<^*>_{q(X, Z, B)}$ expresses that it takes the expected value regarding q (X, Z, B).

[Equation 13]

$$D_{KL} = \left\langle \log \frac{p(X, Z, B \mid D)}{q(X, Z, B)} \right\rangle_{q(X,Z,B)} \quad (13)$$

To make this optimization easy, it is assumed that the test distribution q (X, Z, B) is given by the product of its marginal distribution q (X) and q (Z, B), namely there is dependence between the variable X and {Z, B}. Also, each element of q (X) and q (Z, B) are assumed to be independent among pixels, and further each element q ($x_j$) is assumed to obey the gamma distribution.

Under the conditions described above, q ($Z_j$, $b_j$) consequently becomes the multinomial distribution because the probability variables $Z_j$ and $b_j$ are discrete variables. From above, the test distribution q (X, Z, B) can be expressed by equation that are the equation (14) and the equation (15) below. Note that the alternate optimization as shown by the equation (16) below is performed because it is difficult to optimize test distributions a(x) and q (Z, B) simultaneously.

[Equation 14]

$$q(X, Z, B) = q(X)q(Z, B) \quad (14)$$
$$= \prod_{j=1}^{J} q(x_j)q(z_j, b_j)$$

[Equation 15]

$$q(X) = \prod_{j} \left[ \frac{1}{\Gamma(\alpha_j)} \beta_j^{\alpha_j} x_j^{\alpha_j-1} e^{-\beta_j} \right] \quad (15)$$

[Equation 16]

$$q(X) = \operatorname*{argmin}_{q(X)} D_{KL} \quad (16)$$

[Equation 17]

$$q(z_j, b_j) = \arg\min_{q(z_j,b_j)} D_{KL} \quad (17)$$

Figure 3:

Here, the SCG (Scaled Conjugate Gradient) method was employed for the optimization of the parameters $q(x_j)$ $\alpha_j$, $\beta_j$ in the $q(x_j)$. Under the fixation of the test distribution q (X) and q ($z_j'$, $b_j'$) (note that j' differs from j) other than the j-th pixel, q ($z_j$, $b_j$) that minimizes the KL distance can be analytically found. This analytical solution depends on the neighboring pixel q($z_j'$, $b_j'$) (j'$\epsilon_n$(j)) of j. Thus, in order to renovate the q (Z, B) without changing the distribution of neighboring pixels, the subsets of pixels to become checkered as shown in FIG. 3 are alternately optimized. Namely, the parameter q (Z, B) does not renovate all the pixels simultaneously but optimize the subset of pixels in the checkered patterns shown in the FIG. 3. After renovating q (zj, bj) corresponding to the gray portion in FIG. 3, q ($z_j$, $b_j$) corresponding to pixels in the gray portion is renovated.

Thus far, the X-ray CT image processing method and the X-ray CT image processing program according to the present invention have been explained. In the embodiments below, a computer experiment to study the effectiveness of the present invention is conducted and the screen reconstruction of the X-ray image processing method and the X-ray image processing program are evaluated by comparing these with the screen reconstruction by the conventional technology.

By the evaluation experiment described below, the usefulness of the X-ray CT image processing method and the X-ray CT image processing program according to the present invention will be understood.

In the embodiment, in order to be able to measure the error between the reconstruction image and the genuine image, a proper genuine image was prepared, and against that proper genuine image, the X-ray projection simulation was performed to artificially generate a projection image (sinogram). For the X-ray projection, the energy of the incident X-ray is divided into 5 values, namely 60 keV, 70 keV, 80 keV, 90 keV and 100 keV (the photon numbers for each are 6×10⁴, 2.5×10⁴, 1.5×10³, 7×10³ and 5×10³), in order to consider the energy dependence (wavelength dependence) of the material X-ray absorption coefficient and each divided X-ray was attenuated according to the X-ray absorption coefficient specific for each material. It was assumed that the photon of the attenuated X-ray with addition of a noise (noise) generated according to the Poisson noise was observed at the detector.

In the embodiments 1 and 2 below, the followings were assumed, namely, the number of the detector was 95 (pieces), the resolution of the image was 64×64 (pixels) and the projection interval was 1° between 1° and 180°. In order to quantitatively evaluate the inference quality of the reconstruction image, PSNR (Peak Signal to Noise Ratio) expressed by the equation (18) below was used.

[Equation 18]

$$PSNR = 10\log_{10}\left(\frac{MAX^2}{MSE}\right) \text{ (dB)} \quad (18)$$

In the equation (18) above, MAX is the maximum value of the pixel value and MSE is an average squared error between a true image and a reconstruction image. MSE is smaller with higher PSNR. Namely, the image is nearer to the true image. What is described below is a comparison result of image reconstruction by the following three methods that are, the FBP method, the method to reconstitute the image by the Bayesian inference assuming the prior distribution not considering X-ray energy distribution to follow the Gaussian distribution ("the Conventional method"; hereafter) and the X-ray CT image processing method by discretizing the X-ray energy into 3 energies, according to the present invention ("The present invention method" hereafter), followed by comparison results of each other.

Figure 4:
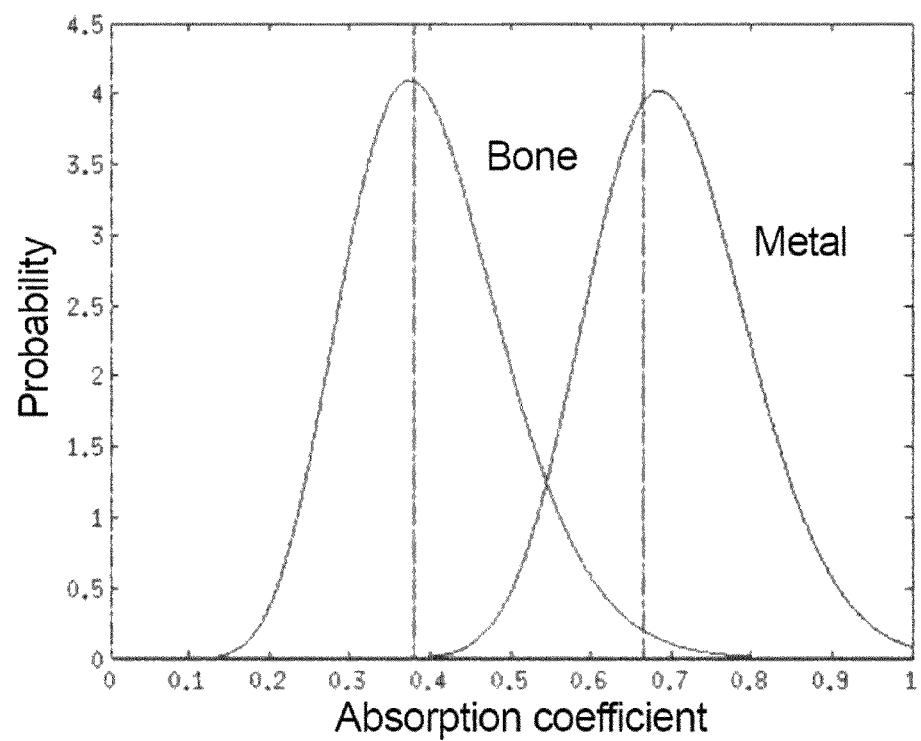

Note that the prior distribution of metal and bone is shown in FIG. 4. FIG. 4 shows the prior distribution of metal and bone and the X-ray absorption coefficient of the true image at 60 keV. The X-ray absorption coefficients of metal and bone are probability distribution expressed by the gamma distribution with 0.7 and 0.4 as average values. The X-ray absorption coefficient of the genuine image is set at a value 5% smaller than the average of the prior distribution.

Embodiment 1

Figure 5:
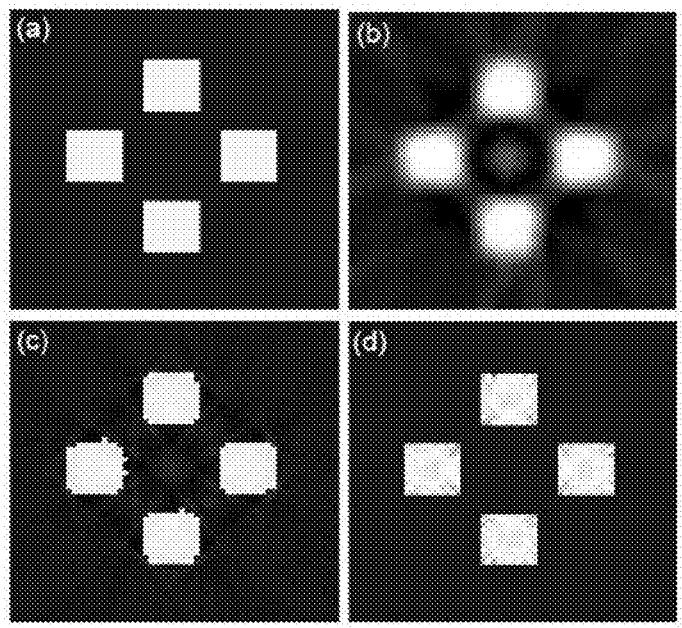

For embodiment 1, a computer experiment regarding the image reconstruction against a phantom including 4 metals is explained referencing FIG. 5.

FIG. 5 (a) is a genuine image, (b) is a reconstruction image by the FBP method, (c) is a reconstruction image by the simple Bayesian method and (d) is the reconstruction image according to the present invention.

In embodiment 1, image reconstruction experiments were conducted on the genuine image as shown in FIG. 5 (a), employing each method, namely the FBP method, the simple Bayesian method and the method in this invention. The sum of the photon number for the incident X-ray was assumed to be 1.12×10⁵, and in the X-ray CT image processing method of the present invention, the X-ray energy was discretized to three intensities, that were 60 keV, 80 keV and 100 keV and the photon numbers belonging to each were set at 7.510⁴, 3×10⁴ and 10 0.7×10⁴, respectively. The repetition number was set both at 25, for comparison. The inference result is shown in FIG. 5 (b) to (d).

Also, PSNR by each FBP method, the simple Bayesian method and the method of the present invention is shown in Table 1 below. It is understood from the table that the PSNR for the FBP method and the simple Bayesian method are larger than the PSNR for the method of the present invention and the present invention method can conduct higher precision inference.

TABLE 1

|  | FBP method | Simple Bayesian method | Present invention method |
|---|---|---|---|
| PSNR (dB) | 16.7489 | 22.3419 | 27.3353 |

Embodiment 2

Figure 6:
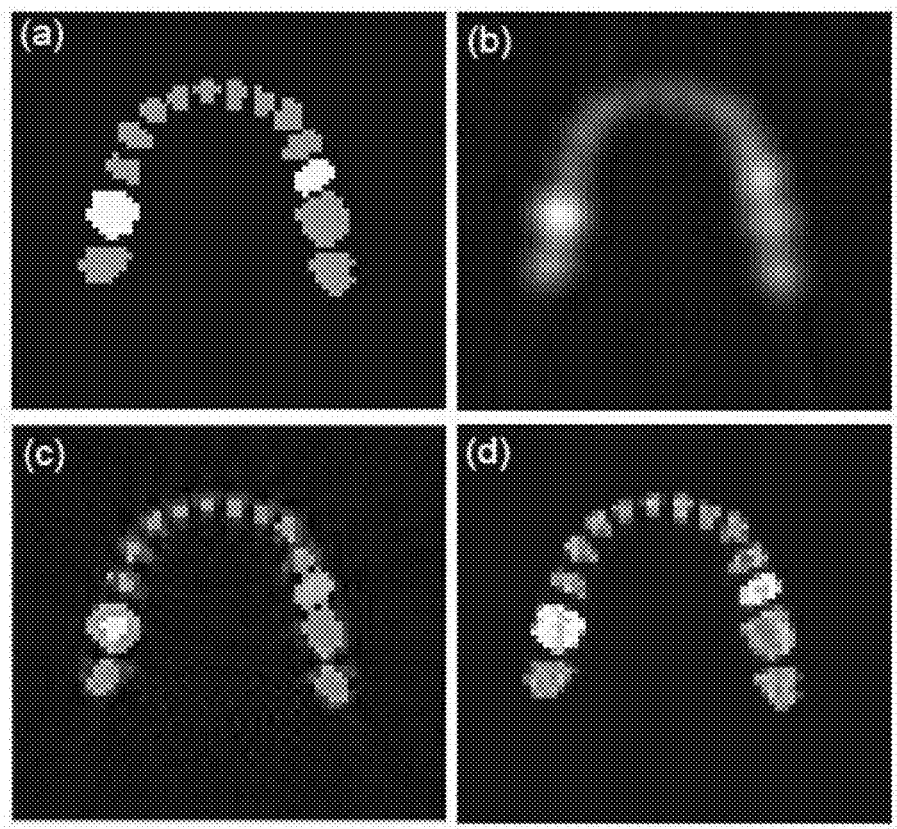

For embodiment 2, a computer experiment regarding the image reconstruction against a phantom of teeth including a metal implant is explained referencing FIG. 6.

FIG. 6 (a) is an genuine image, (b) is a reconstruction image by the FBP method, (c) is a reconstruction image by the simple Bayesian method and (d) is the reconstruction image according to the present invention.

In embodiment 2, image reconstruction experiments were conducted on the genuine image as shown in FIG. 5 (a), employing each method, namely the FBP method, the simple Bayesian method and the method in this invention. The sum of the photon number for the incident X-ray was assumed to be $1.12 \times 10^5$, and in the X-ray CT image processing method of the present invention, the X-ray energy was discretized to three intensities, that were 60 keV, 80 keV and 100 keV and the photon numbers belonging to each were set at $7.510^4$, $3 \times 10^4$ and $10\ 0.7 \times 10^4$, respectively. The repetition number was set both at 25, for comparison. The inference result is shown in FIG. 5 (b) to (d).

Also, PSNR at each FBP method such as, simple Bayesian method and the method of the present invention is shown in Table 1 below. It is understood from the table that the PSNR for FBP method and simple Bayesian method is larger than the PSNR for the method of the present invention and the method of present invention can conduct higher precision inference.

TABLE 2

|  | FBP method | Simple Bayesian method | Present invention method |
|---|---|---|---|
| PSNR (dB) | 16.6327 | 21.5578 | 25.1628 |

As was explained above, it was shown that various artifacts originating to the influence of the beam hardening can be reduced by considering the energy distribution of the X-ray spectrum and estimating X-ray absorption coefficient with energy dependence (wavelength dependence) based on the statistic model. As the computer experiments according to embodiments 1 and 2, only those cases where the X-ray energy was divided into three energies were selected. However, it can be seen that the artifacts were extensively reduced even when the number of the discrete representation is smaller than the partition number of the accrual energy. Furthermore, it would be possible to conduct a better estimation by further increasing the partition number of the energy.

Embodiment 3

Next, regarding the observation process of the projected X-ray observation, it will be explained that the multiple-X-ray sum can express the phenomena in which multiple X-rays of different spatial positions, directions and wavelengths are incident on the detector under the conditions that the detection surface of the detector possesses a spatially finite area, the detection time of the X-ray at the detector has a finite width and the X-ray possesses a wavelength region (a spectral distribution) having a finite expanse.

Figure 7:
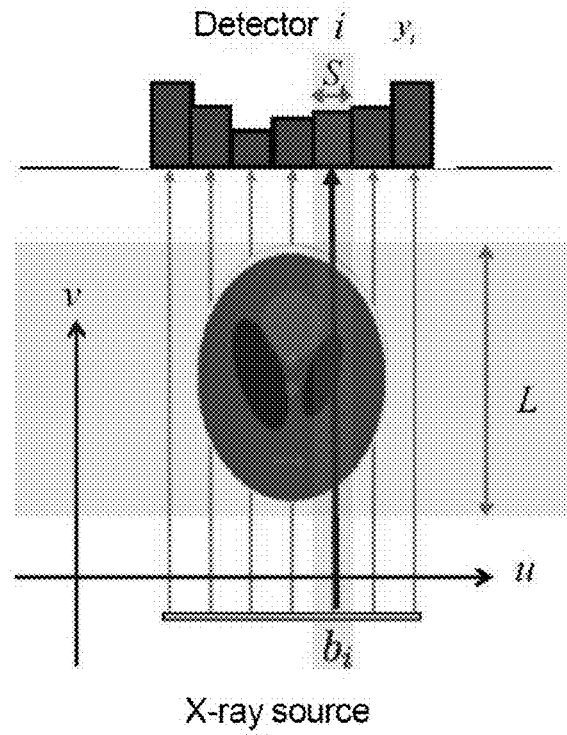

Firstly, an explanation is given by referencing FIG. 7 with a parallel beam as an example. A projection by a parallel beam in a 2 dimensional plane as shown in FIG. 7 is assumed. Here, the direction of the X-ray radiation is defined as the y-axis and the direction orthogonal thereto is defined as the u-axis. Variables are defined as below in this coordinate system.

The X-ray absorption coefficient of a material at a position (u, v) for a wavelength $\lambda$ is to be expressed by x (u, v, $\lambda$). Note that the material is assumed to be included in v∈L.

Let the photon number incident on the detection surface $S_i$ of the i-th detector be $y_i$ ($\lambda$). Let the photon number of a wavelength $\lambda$ radiated per unit time and unit area by the X-ray source of a parallel beam be d ($\lambda$) and let an average number of electrons excited by one photon of a wavelength $\lambda$ be $\rho$ ($\lambda$).

Under this condition, the expected value of the current $Y_i$ observed by the i-th detector per unit time is expressed by the equation (19) below. Furthermore, in a case where current accumulated for a specific time duration is observed, the time integral of the current is to be performed.

[Equation 19]

$$Y_i = \int \rho(\lambda) y_i(\lambda) d\lambda$$

$$y_i(\lambda) = \int_{u \in S_i} d(\lambda) \exp(-\int_{v \in L} x(u,v,\lambda) dv) du \quad (19)$$

It is understood that artifacts are generated if the estimation method that assumes a line integral is employed in a case where a spatial expanse of the detection surface and an expanse of X-ray spectral distribution exist because the formula (19) above cannot arrive at a line integral (an integral regarding v described above) assumed by a reverse projection method according to the formula (19) above. Similarly, in a case where rotation is considered at a time when the detector receives a light, the formula (19) prevents the arrival at the line integral. Approximation of integral by sum is considered because the calculation by the multiple integral mentioned above is difficult. It is shown that the above leads to a consideration on a multiple-X-ray sum. Firstly, the integral regarding u, v in the formula (20) below is replaced to a sum, noting only on a specific wavelength in the formula (19) above.

[Equation 20]

$$y_i = \int_{u \in S_i} d \exp(-\int_{v \in L} x(u,v) dv) du \quad (20)$$

[Equation 20]

$$y_i = \int_{u \in S_i} d \exp(-\int_{v \in L} x(u,v) dv) du \quad (20)$$

Figure 8:
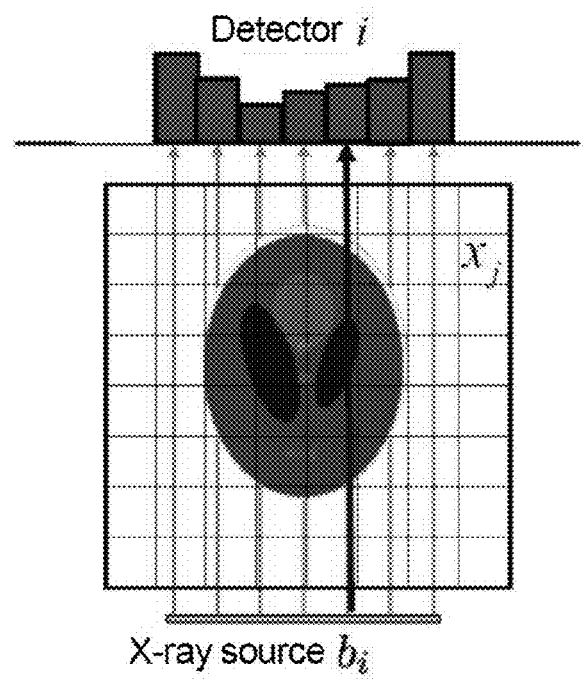

In order to approximately express the integral regarding u and v above on computer, a discretization is performed. (Refer to FIG. 8) When the space is discretized along u axis and v axis, the integral regarding v in the equation (20) above can be approximated following the equation (21) below.

[Equation 21]

$$\int_{v \in L} x(u,v) dv \approx \Sigma_{j \in I(u)} x_j \Delta L \quad (21)$$

Here, $X_j$ is the X-ray absorption coefficient of the i-th pixel, $I(u)$ expresses the set of pixel index placed at the position u on the u axis and $\Delta L$ expresses the length of one side of the pixel. When the length of one side of the pixel is expressed by $\Delta L=1$, the equation (21) above is expressed by the equation (22) below.

[Equation 22]

$$\int_{v \in L} x(u,v) dv \approx \Sigma_{j \in I(u)} x_j \quad (22)$$

Accordingly, when the length of one side of the pixel is 1, $y_i$ is expressed by the equation (23) below and further, when an integral regarding a ray (an integral regarding u) incident on the same detector is approximated by the sum, $y_i$ is expressed by the equation (24) below.

[Equation 23]

$$y_i = \int_{u \in S_i} d\exp\left(-\int_{v \in L} x(u,v) dv\right) du \approx \int_{u \in S_i} d\exp\left(-\sum_{j \in I(u)} x_j\right) du \quad (23)$$

[Equation 24]

$$\approx \sum_{\{k | u_0 + \frac{k}{N} \in S_i\}} \frac{1}{N} d\exp\left(-\sum_{j \in I(u_0 + \frac{k}{N})} x_j\right) \quad (24)$$

1/N is the rectangle width for the approximation of integral by thin rectangles.)

In the equation (24) above, 1/N represents the width of a rectangle when the integral is approximated by cutting out rectangles.

This corresponds to thinking of the sum of projection expressed by a linear integral about the index k.

As has been explained thus far, it is known that the multiple X-ray needs to be considered when the spatial expanse of the detector is taken into account.

Figure 9:
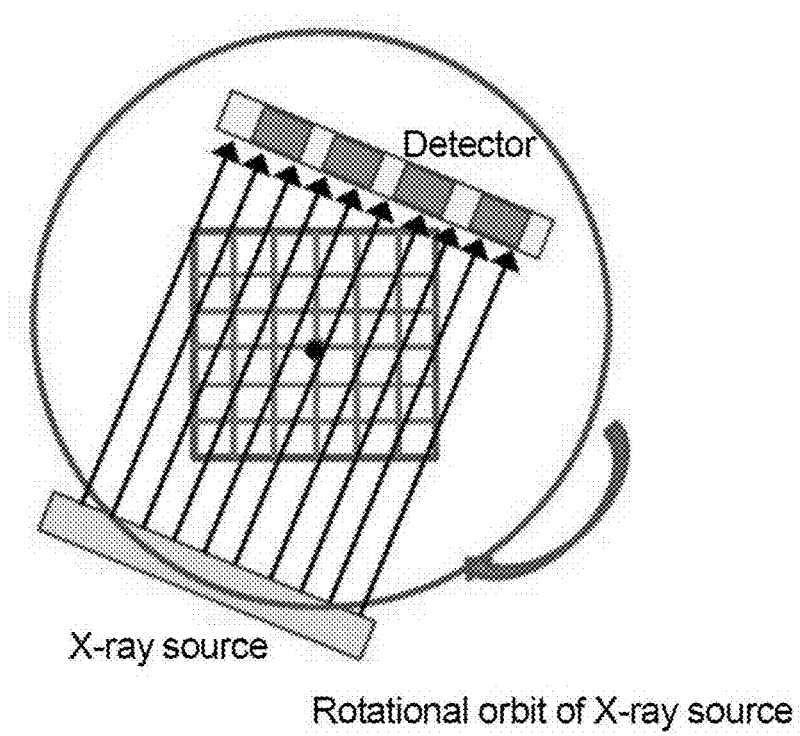

The above assumes a case where the X-ray is incident on the pixel directly. However, for an equipment in which the X-ray source and the detector rotate facing each other (refer to FIG. 9) such as in an ordinary X-ray CT equipment, it is necessary to anticipate a situation where the X-ray is radiated at the pixel obliquely.

In this case, the equation (24) above about the projection can be expressed by generalizing the equation (24) unto the following equation (25) below.

[Equation 25]

$$y_i \approx \sum_{\{k | u_0 + \frac{k}{N} \in S_i\}} \frac{1}{N} d\exp\left(-\sum_{j \in I(u_0 + \frac{k}{N})} x_j\right) \quad (25)$$

[Equation 26]

$$y_i \approx \sum_{\{k | r(k) \in S_i\}} d\exp\left(-\sum_{j \in I_k} l_{kj} x_j\right) \Delta N \quad (26)$$

Here, $\Delta N = 1/N$, $r(k)$ expresses the position of a beam k on the detection surface and $\{k | r(k) \in S_i\}$ expresses the aggregation of beams reaching the detector j. $I_k$ expresses the index aggregation of the pixel the beam k intersects and $l_{kj}$ expresses the intersection length of the beam k and the pixel j. The equation (25) above can be considered to be the case that $l_{kj}$ in the equation (26) above is assumed to be 1.

Regarding the equation (26) above, a similar equation holds by computing $l_{kj}$ considering the beam direction even for a fan beam or a corn beam besides a parallel beam.

What the above formula (26) suggests is the necessity to consider the projection by each beam that transmits the detection surface when an observation model of the projection considering the detection surface expansion is taken into account.

When the sum of $l_{kj} x_j$ in the equation (26) above is written altogether regarding the detector i and the beam k, it can be expressed by a matrix operation such as Lx. The case in which the matrix L is (the number of the detector)×(the pixel number of the reconstruction image) when the detection surface expansion is not considered changes to another case in which the matrix L becomes (the number of beams that transmits the detector) x (the pixel number of the reconstruction image) when the detection surface expansion is considered. While the greater the beam number is, the higher the integral precision becomes, a problem arises that the calculation volume increases.

Next, a rotation during the projection (an integral about time) is assumed. First of all, if the photon number observed at a time t is assumed to be $y_{i,t}$, it can be expressed by the equation (27) below.

[Equation 27]

$$y_{i,t} = \sum_{\{k | r(k) \in S_i\}} d\exp\left(-\sum_{j \in I_k} l_{kj}^{(t)} x_j\right) \Delta N \quad (27)$$

The photon number detected during the detection time (the exposure time) of the detector becomes the integral of $y_{i,t}$ about time and accordingly can be expressed by the equation (28) below.

[Equation 28]

$$\int_{t \in T} y_{i,t} dt \quad (28)$$

Regarding the equation (28) above, when the integral about time is replaced by the sum, the expression by the equation (29) below becomes available.

[Equation 29]

$$\Sigma_{\{k | r(k) \in T\}} y_{i,r(k)} \Delta t \quad (29)$$

The photon $y_{i,t}$ incident on the detector at each time t is expressed by the sum of bundles of multiple rays as is shown in the equation (28) above when the detection surface expansion is considered. The integral about time is equivalent to thinking of a sum regarding a new bundle of rays because a further sum is included. Therefore, the photon number measured during the detection time T (the exposure time) can be expressed by the equation (30) below when the set S of ray indices is expressed by $S_{j,t}$ which is time dependent and the set $I_k$ of pixel indices each ray k transmits through is redefined.

[Equation 30]

$$\sum_{\{k | r(k) \in S_{i,T}\}} d\exp\left(-\sum_{j \in I_k} l_{kj} x_j\right) \Delta N \quad (30)$$

The expression by the equation (31) below holds when the integral about the wavelength in the equation (30) above is replaced by a sum.

[Equation 31]

$$Y_i = \sum_m y_{i,t}(\lambda_m)\Delta\lambda \quad (31)$$

When the explanation given thus far is summed up, it is known that the number of photons observed can be expressed by the equation (32) below, when the surface expansion, the rotation during the projection and the X-ray wavelength dependence are taken into account. Here, $b_m = d_m \rho_m$.

[Equation 32]

$$\overline{Y}_i \approx \sum_m \sum_{\{k|r(k) \in S_{i,t}\}} b_m \exp\left(-\sum_{j \in l_k} l_{kj} x_{jm}\right) \Delta N \Delta\lambda \quad (32)$$

Summing about m and k outside the exponential as expressed in the above formula (32) is called the multiple-X-ray sum. This cannot be expressed by a liner integral that does not assume the existence of a sum (or integral) outside the exponential. The algorithm based on the Bayesian inference disclosed in the specification of the present invention can be applied to observation process, in general, including such multiple X-ray summation.

INDUSTRIAL APPLICABILITY

The present invention is useful not only for medical purpose but for industrial X-ray CT equipment that decreases beam hardening artifacts. Also, it is useful for belt conveyer type X-ray CT equipment that cannot ignore the shift and the rotation by a belt conveyer and the dental X-ray CT equipment.

The invention claimed is:

1. An X-ray CT image processing method for visualizing the inside of a scanned object in a form of a spatial distribution of X-ray absorption coefficients based on projection X-ray data obtained by detection of at least one projected X-ray at one or more X-ray detectors under several X-ray projections on an observation object, comprising:
   setting a probability distribution of a projection X-ray at an observation process in a case of said observation process wherein projection X-rays detected by an X-ray detector include a sum of multiple projection X-rays incident on spatially different positions, the multiple projection X-rays being incident at temporally different timings and including multiple projection X-rays of different wavelengths;
   setting a prior probability distribution regarding an X-ray absorption coefficient of a material inside the observation object, using a parameter concerning the material;
   computing a joint posterior distribution of X-ray absorption coefficient and said material's parameter, the joint posterior distribution computed from said projection X-ray data, said prior probability distribution, and said observation process; and
   estimating an X-ray absorption coefficient based on the said joint posterior distribution.

2. An X-ray CT image processing method as set forth in claim 1, further comprising:
   approximating said posterior distribution of X-ray absorption coefficient with a test distribution using the said observation process and said prior distribution so that the distributional distance between said posterior distribution and the test distribution is small; and
   consequently computing an expected value of the test distribution regarding said X-ray absorption coefficient.

3. An X-ray CT image processing method as set forth in claim 1, wherein a sum of projected X-rays of different X-ray wavelengths is included in a sum of said multiple projection X-rays, and a prior probability distribution regarding the wavelength dependent X-ray absorption coefficients of each pixel is set using a parameter for expressing a distribution of an X-ray absorption coefficient for each said material and each X-ray wavelength.

4. An X-ray CT image processing method as set forth in claim 1, wherein a sum of the projection X-rays of different X-ray wavelengths is included in a sum of said multiple projection X-rays, and an X-ray absorption coefficient possessing a wavelength dependence of each pixel is set as a product of an X-ray absorption coefficient density not depending on the wavelength and an X-ray absorption coefficient ratio among X-ray wavelengths specified for each said material, not depending on a pixel, the method comprises using a parameter for expressing an X-ray absorption coefficient ratio among X-ray wavelengths specified for each said material, and the prior probability distribution of X-ray absorption coefficient possessing wavelength dependence of each pixel is set by a prior probability distribution conditional to said X-ray absorption coefficient density of each pixel under a condition of said material and a prior probability distribution for said material.

5. An X-ray CT image processing method as set forth in claim 3, wherein a prior probability distribution for said material is set by a prior probability distribution expressed by a parameter for representing the content percentage of each material and a parameter for showing an extent of spatial continuity of each material.

6. An X-ray CT image processing method as set forth in claim 4, wherein a conditional prior probability distribution of said X-ray absorption coefficient density specified for each said material is set by a conditional prior probability distribution of said X-ray absorption coefficient density specified for each subclass of each material and a mixed probability distribution resulting from a sum regarding all attainable subclasses of each material for a product of a conditional prior probability distribution of a subclass of each material, and a prior probability distribution of subclass for said each material is set by a parameter for showing appearance extent of a subclass for each material and a parameter for showing the spatial continuity extent of a subclass for each said material.

7. An X-ray CT equipment for imaging an inside of an observation object as a spatial distribution of an X-ray absorption coefficient based on projection X-ray data obtained by detecting a projected X-ray on an X-ray detector after projecting an X-ray on an observation object, the X-ray CT equipment comprising:
   a means for setting a probability distribution of projection X-rays at an observation process in a case where a projection X-ray detected by an X-ray detector is a sum of any or all of three types of multiple X-rays: (1) multiple projection X-rays incident on spatially different positions, (2) multiple projection X-rays incident at temporally different timings, and (3) multiple projection X-rays of different wavelengths;
   a means for setting a prior probability distribution regarding a parameter for expressing an X-ray absorption coefficient of a material constituting an inside of an observation object and a material; and a means for estimating a spatial distribution of said X-ray absorption coefficient by estimating a posterior probability distribution regarding said X-ray absorption coefficient and said material from said projection X-ray data, a probability distribution expressing a likelihood of said projection X-ray data and said prior probability distribution.

8. An X-ray CT equipment comprising:

an X-ray detection mechanism including at least one X-ray detector;

a computer which executes an image processing program that performs a method to assist imaging an inside of an observation object as a spatial distribution of X-ray absorption coefficients based on projection X-ray data obtained by detecting projected X-rays at the X-ray detection mechanism by projecting an X-ray on an observation object in an observation process, the method comprising (a) setting a probability distribution of a projection X-ray wherein a projection X-ray detected by the X-ray detection mechanism is a sum of multiple X-rays consisting of at least one projection X-ray chosen from multiple projection X-rays to be detected by the X-ray detection mechanism incident on a spatially different positions to a detection plane of the X-ray detection mechanism, multiple projection X-rays incident at temporally different timings and multiple projection X-rays of different wavelengths, (b) setting a prior probability distribution regarding a parameter for expressing an X-ray absorption coefficient of a material constituting an inside of an observation object and said material, and (c) estimating a spatial distribution of said X-ray absorption coefficients by estimating a posterior probability distribution regarding said X-ray absorption coefficient and said material from said projection X-ray data from said projection X-ray data and a probability distribution of a projection X-ray at said observation process and said prior probability distribution.

9. An X-ray CT equipment as set forth in claim 8, wherein said X-ray absorption coefficient estimation comprises calculating a test distribution regarding said X-ray absorption coefficient and said material from a probability distribution of a projection X-ray at said observation process and said prior probability distribution for making said posterior distribution and inter distribution distance thereof small; and the method comprises estimating an expected value of test distribution regarding said X-ray absorption coefficient.

* * * * *